United States Patent
Chen et al.

(10) Patent No.: US 10,487,303 B2
(45) Date of Patent: Nov. 26, 2019

(54) AUTOMATIC OFF-LINE GAS-WATER COMBINED-WASHING MEMBRANE BIOREACTOR (MBR)

(71) Applicant: GUANGZHOU GUANGSHEN ENVIRONMENTAL SCI-TECH CO., LTD., Guangzhou (CN)

(72) Inventors: Xinyi Chen, Guangzhou (CN);
Shanglong Wen, Guangzhou (CN);
Jianyun Shi, Guangzhou (CN);
Yanfang Zhang, Guangzhou (CN);
Haochun Zhang, Guangzhou (CN)

(73) Assignee: Guangzhou Guangshen Environmental Sci-Tech Co., Ltd., Guangzhou (CN)

( * ) Notice: Subject to any disclaimer, the term of this patent is extended or adjusted under 35 U.S.C. 154(b) by 0 days.

(21) Appl. No.: 15/504,289

(22) PCT Filed: Aug. 3, 2016

(86) PCT No.: PCT/CN2016/093057
§ 371 (c)(1),
(2) Date: Feb. 15, 2017

(87) PCT Pub. No.: WO2017/121106
PCT Pub. Date: Jul. 20, 2017

(65) Prior Publication Data
US 2018/0340143 A1 Nov. 29, 2018

(30) Foreign Application Priority Data
Jan. 14, 2016 (CN) .......................... 2016 1 0029641

(51) Int. Cl.
*C12M 1/00* (2006.01)
*B01D 65/02* (2006.01)
(Continued)

(52) U.S. Cl.
CPC ............. *C12M 47/18* (2013.01); *B01D 61/14* (2013.01); *B01D 61/18* (2013.01); *B01D 61/22* (2013.01);
(Continued)

(58) Field of Classification Search
CPC ...................................................... C12M 47/18
(Continued)

(56) References Cited

U.S. PATENT DOCUMENTS 5,192,456 A * 3/1993 Ishida .................... B01D 61/14
210/195.2

OTHER PUBLICATIONS

International Search Report, for PCT/CN2016/093057, 3 pages, dated Oct. 27, 2016.

* cited by examiner

*Primary Examiner* — Kevin Joyner
*Assistant Examiner* — Holly M Mull
(74) *Attorney, Agent, or Firm* — Billion & Armitage; Benjamin C. Armitage

(57) ABSTRACT

The invention discloses an automatic off-line gas-water combined-washing membrane bioreactor, comprising a PLC automation control cabinet, a MBR reactor, a MBR membrane assembly, a rotating hood, an annular guide rail, a lifting device, a washing pipe network, an external interface, a gas washing pipe, a water washing pipe, a gas pump and a water pump, wherein the gas pump, the water pump and the three-way change valve are all connected with the PLC automation control cabinet, the washing pipe network is provided with several nozzles. The present invention adopts a full PLC automation control system, the PLC automation control cabinet controls a pressure washing pump (gas pump and water pump), and gas or water is injected into the washing pipe network by flexibly adjusting the three-way
(Continued)

change valve, so that the operation is simple, the cleaning is complete, and the manual operation load is reduced.

8 Claims, 1 Drawing Sheet

(51) Int. Cl.
*C02F 3/12* (2006.01)
*B01D 61/14* (2006.01)
*B01D 61/18* (2006.01)
*B01D 61/22* (2006.01)

(52) U.S. Cl.
CPC ........... *B01D 65/02* (2013.01); *B01D 65/025* (2013.01); *C02F 3/1273* (2013.01); *B01D 2311/2642* (2013.01); *B01D 2321/04* (2013.01); *B01D 2321/18* (2013.01); *B01D 2321/40* (2013.01); *C02F 2303/16* (2013.01); *Y02W 10/15* (2015.05)

(58) Field of Classification Search
USPC ...................................................... 435/287.1
See application file for complete search history.

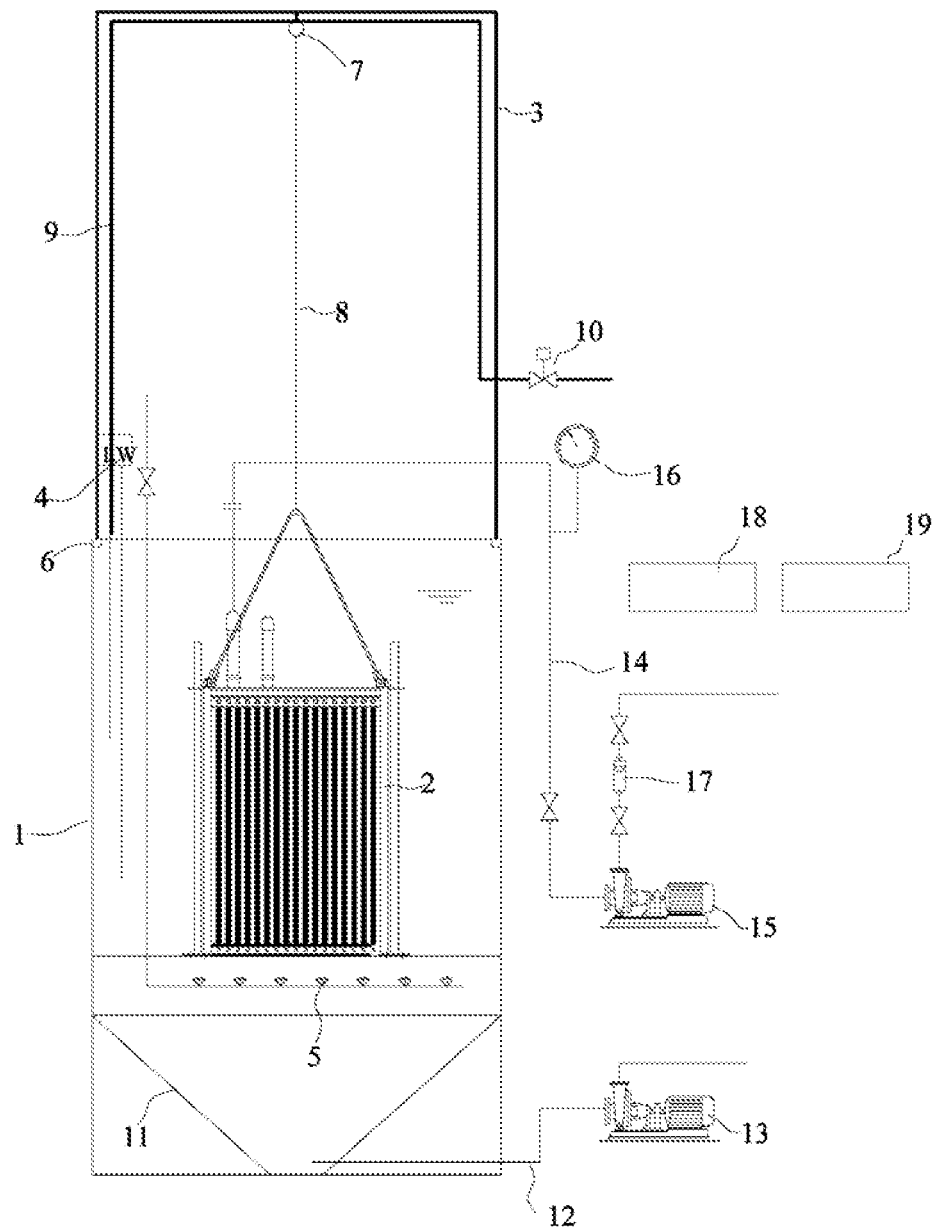

AUTOMATIC OFF-LINE GAS-WATER COMBINED-WASHING MEMBRANE BIOREACTOR (MBR)

CROSS-REFERENCE TO RELATED APPLICATION(S)

This application is a 371 of PCT/CN2016/093057, filed on 3 Aug. 2016, which claims priority to Chinese Application No. 201610029641.9, filed on 14 Jan. 2016.

FIELD OF THE INVENTION

The present invention relates to the field of sewage disposal technology, and more particularly, relates to an automatic off-line gas-water combined-washing membrane bioreactor (MBR).

BACKGROUND OF THE INVENTION

Membrane bioreactor (Membrane Bioreactor-MBR) treatment process is an emerging water treatment technology, which organically combines a traditional sewage biological treatment process with a membrane separation technology, and has been successfully applied to sewage treatment. The membrane bioreactor generally consists of a membrane separation assembly and a bioreactor. For the general membrane bioreactor, the membrane assembly is placed in the bioreactor, which usually can reach a high chemical oxygen demand (COD) removal rate by isolating high concentration activated sludge The design of the membrane bioreactor is focused on a set of highly efficient membrane cleaning system, with alternative methods including water backwash, gas washing, and chemical agent cleaning, etc. In the prior art, the off-line washing of the MBR membrane bioreactor has problems that difficult to be cleaned, cumbersome manual operation, incomplete cleaning and poor recovery performance, etc.

SUMMARY OF THE INVENTION

In order to solve the above problems, the present invention provides an automatic off-line gas-water combined-washing membrane bioreactor (MBR), which is operated simply and washed completely, as well as reduced manual operating loads.

In order to solve the technical problems thereof, the present invention employs the technical solution as follows: an automatic off-line gas-water combined-washing membrane bioreactor (MBR) comprises a PLC automation control cabinet, a MBR reactor, a MBR membrane assembly arranged in the MBR reactor and a rotating hood arranged at the top of the MBR reactor, wherein an annular guide rail is arranged at the top of the MBR reactor, the rotating hood is rotatably arranged on the annular guide rail, a lifting device capable of lifting the MBR membrane assembly to elevate it to the inside of the rotating hood is arranged above the MBR reactor, a washing pipe network is arranged on an inner wall of the rotating hood, the washing pipe network is provided with an external interface at an outer side of the rotating hood, the external interface is connected with a gas washing pipe and a water washing pipe by a three-way change valve, the gas washing pipe is externally connected with a gas pump, the water washing pipe is externally connected with a water pump, the three-way change valve is a magnetic exchange valve, the gas pump, the water pump and the three-way change valve are all connected with the PLC automation control cabinet, the washing pipe network is provided with several nozzles obliquely pointing to the inside of the rotating hood, and the nozzles can produce a reactive thrust applied to drive the rotating hood to rotate along the annular guide rail when ejecting gas or water.

Further as an improvement of the technical solution of the present invention, a microporous aerator is arranged below the MBR membrane assembly in the MBR reactor.

Further as an improvement of the technical solution of the present invention, a sludge pipe is arranged at the bottom of the MBR reactor, the sludge pipe is provided with a sludge pump outside the MBR reactor, and the sludge pump is connected with the PLC automation control cabinet.

Further as an improvement of the technical solution of the present invention, a tapered sludge tank is formed at the bottom of the MBR reactor.

Further as an improvement of the technical solution of the present invention, the MBR membrane assembly is externally connected with a water producing pipe, the water producing pipe is provided with a water producing pump outside the MBR reactor, and the water producing pump is connected with the PLC automation control cabinet.

Further as an improvement of the technical solution of the present invention, a negative pressure gauge is arranged on the water producing pipe between the MBR membrane assembly and the water producing pump, the water producing pipe externally connected with the water producing pump is provided with a water producing flowmeter, and the negative pressure gauge is connected with the PLC automation control cabinet.

Further as an improvement of the technical solution of the present invention, a liquid level meter is arranged in the MBR reactor.

Further as an improvement of the technical solution of the present invention, the lifting device comprises a winding engine, a diverting pulley arranged above the MBR reactor and a pulling cable connected with the MBR membrane assembly after introducing by the winding engine and passing around the diverting pulley, a travel switch is arranged at the bottom of the diverting pulley, and both the winding engine and the travel switch are connected with the PLC automation control cabinet.

The present invention has the advantageous effects that: the membrane bioreactor is controlled by a full PLC automation control system, the PLC automation control system controls the lifting device to lift the MBR membrane assembly in the MBR reactor to access to an automatic off-line high-pressure washing stage; the MBR membrane assembly stops lifting until being lifted into the rotating hood, at this moment, the PLC automation control cabinet feeds back to a pressure washing pump (gas pump and water pump), gas or water is injected into the washing pipe network by flexibly adjusting the three-way change valve, the rotating hood automatically rotates under the function of a reactive thrust when the nozzle ejects the gas or water, so that the ejected gas or water washes the MBR membrane assembly completely without a dead angle; a gas-water combined-washing mode is adopted in the present invention, the washing mode can be firstly gas washing, water washing and then water-gas combined-washing, also can be firstly water washing, gas washing and then water-gas combined-washing, or can be water-gas combined-washing and then water washing and gas washing in a separate way, various orders are not limited on the basis of washing clean. An automatic cleaning device is arranged in the traditional MBR membrane reactor, which realizes automatic washing without manual operation, so that manual operation load is reduced due to full automatic washing; an automatic rotating device is used as the washing device, realizing washing in all directions at 360° without a dead angle; and the gas-water combined-backwashing mode is adopted to realize the flexible combination of a plurality of washing modes.

BRIEF DESCRIPTION OF THE DRAWINGS

The present invention is further illustrated with reference to drawings thereinafter.

FIG. 1 is a structural schematic diagram of the present invention.

DETAILED DESCRIPTION OF THE EMBODIMENTS

Referring to FIG. 1, it shows the specific structure of the preferable embodiment of the present invention. The structure feature of various elements of the present invention will be illustrated in details hereinafter; while if describing directions (up, down, left, right, front and rear), a structure as shown in FIG. 1 is referred description, but the actual directions used in the present invention are not limited to these.

The present invention provides an automatic off-line gas-water combined-washing membrane bioreactor (MBR), comprising a MBR reactor 1, a MBR membrane assembly 2 arranged in the MBR reactor 1 and a rotating hood 3 arranged at the top of the MBR reactor 1, wherein a liquid level meter 4 is arranged in the MBR reactor 1, and a microporous aerator 5 is arranged below the MBR membrane assembly 2 in the MBR reactor 1. An annular guide rail 6 is arranged at the top of the MBR reactor 1, the rotating hood 3 is rotatably arranged on the annular guide rail 6, a wheel set or a lubricating oil film is arranged between the rotating hood 3 and the annular guide rail 6, a lifting device capable of lifting the MBR membrane assembly 2 to elevate it to the inside of the rotating hood 3 is arranged above the MBR reactor 1, the lifting device comprises a winding engine, a diverting pulley 7 arranged above the MBR reactor 1 and a pulling cable 8 connected with the MBR membrane assembly 2 after introducing by the winding engine and passing around the diverting pulley 7, and the winding engine can lift up or down the MBR membrane assembly 2 through the pulling cable 8. A washing pipe network 9 is arranged on an inner wall of the rotating hood 3, the washing pipe network 9 is provided with an external interface at an outer side of the rotating hood 3, the external interface is connected with a gas washing pipe and a water washing pipe by a three-way change valve 10, the gas washing pipe is externally connected with a gas pump, the water washing pipe is externally connected with a water pump, the washing pipe network 9 is provided with several nozzles obliquely pointing to the inside of the rotating hood, and the nozzles can produce a reactive thrust applied to drive the rotating hood 3 to rotate along the annular guide rail 6 (clockwise or anticlockwise) when ejecting gas or water.

A tapered sludge tank 11 is formed at the bottom of the MBR reactor 1, and sludge produced by water treatment is deposited in the sludge tank 11. A sludge pipe 12 is arranged at the bottom of the MBR reactor 1 the sludge pipe 12 is provided with a sludge pump 13 outside the MBR reactor 1, and the sludge pump 13 discharges the sludge in the sludge tank 11 continuously or intermittently.

The MBR membrane assembly 2 is externally connected with a water producing pipe 14, and the water producing pipe 14 is provided with a water producing pump 15 outside the MBR reactor 1. A negative pressure gauge 16 is arranged on the water producing pipe 14 between the MBR membrane assembly 12 and the water producing pump 15, and the water producing pipe 14 externally connected with the water producing pump 15 is provided with a water producing flowmeter 17.

The three-way change valve 10 is a magnetic exchange valve, the membrane bioreactor further comprises a PLC automation control cabinet 18 and a travel switch arranged at the bottom of the diverting pulley 7, and the winding engine, the negative pressure gauge 16, the water producing pump 15, the sludge pump 13, the travel switch, the gas pump, the water pump and the three-way change valve 10 are all connected with the PLC automation control cabinet 18.

The device is controlled by a full PLC automation control system, a signal of the negative pressure gauge 16 is linked with the winding engine of the lifting device, the water producing pump 15 works, an alarm 19 automatically gives an alarm when a pressure date of the negative pressure gauge 16 reaches a set value, the other accessory devices (such as the water producing pump 15, the sludge pump 13 and the like) of the MBR are stopped at this moment, the signal of the negative pressure gauge 16 is fed back to the PLC automation control cabinet 18, a signal of an automatic control system is fed back to the lifting device to access to an automatic off-line high-pressure washing stage; the MBR membrane assembly 2 is lifted by the winding engine to a certain altitude and stops lifting up until touching the travel switch, the travel switch feeds back a signal to the PLC automation control cabinet 18 at this moment, the PLC automation control cabinet 18 feeds back the signal to a pressure washing pump (gas pump and water pump), the pressure washing pump is started, an automatic backwash program starts, automatic backwash water washing is performed for 8 min, the water pump stops, automatic gas washing starts for 2 min, the time can be adjusted flexibly; the rotating hood 3 automatically rotates under the function of a reactive thrust when the nozzle ejects the gas or water, so that the washing is performed completely without a dead angle; a gas-water combined-washing mode is adopted in the present invention, the washing mode can be firstly gas washing, water washing and then water-gas combined-washing, also can be firstly water washing, gas washing and then water-gas combined-washing, or can be water-gas combined-washing and then water washing and gas washing in a separate way, various orders are not limited on condition that the final washing is clean.

After washing completely, the PLC automation control cabinet starts the lifting device according to the set process, the MBR membrane assembly 2 is dropped down, which can rerun the system. The present invention adopts the PLC programming setting, the system washing completion is executed by a PLC automatic control program, thus reducing a personal error; the system is combined-controlled by the transmission of the negative pressure gauge 16 and the liquid level meter 4, thereby reducing a program error; the alarm 19 can alert various running programs of the system, thus reminding the operator of paying attention to the running state of the system, and solving the emergent problem in time.

Obviously, the present invention is not limited to the above implementation manner. Equivalent modifications or substitutions can further be made by those skilled in the art without departing from the spirit of the present invention and shall all fall within the scope limited by the claims of the present application.

What is claimed is:

1. An automatic off-line gas-water combined-washing membrane bioreactor (MBR) comprising:
   a PLC automation control cabinet,
   a MBR reactor,
   a MBR membrane assembly arranged in the MBR reactor, and
   a rotating hood arranged at the top of the MBR reactor, wherein,
      an annular guide rail is arranged at the top of the MBR reactor, with the rotating hood rotatably arranged on the annular guide rail,
      a lifting device capable of lifting the MBR membrane assembly to elevate it to the inside of the rotating hood is arranged above the MBR reactor,
      a washing pipe network is arranged on an inner wall of the rotating hood, which is provided with an external interface at an outer side of the rotating hood,
      the external interface is connected with a gas washing pipe and a water washing pipe by a three-way change valve,
      the gas washing pipe is externally connected with a gas pump, and the water washing pipe is externally connected with a water pump,
      the three-way change valve is a magnetic exchange valve,
      the gas pump, the water pump and the three-way change valve are all connected with the PLC automation control cabinet,
      the washing pipe network is provided with several nozzles obliquely pointing to the inside of the rotating hood, and
      the nozzles can produce a reactive thrust to drive the rotating hood to rotate along the annular guide rail when ejecting gas or water.

2. The automatic off-line gas-water combined-washing membrane bioreactor (MBR) according to claim 1, characterized in that: a microporous aerator is arranged below the MBR membrane assembly in the MBR reactor.

3. The automatic off-line gas-water combined-washing membrane bioreactor (MBR) according to claim 1, characterized in that: a sludge pipe is arranged at the bottom of the MBR reactor, the sludge pipe is provided with a sludge pump outside the MBR reactor, and the sludge pump is connected with the PLC automation control cabinet.

4. The automatic off-line gas-water combined-washing membrane bioreactor (MBR) according to claim 3, characterized in that: a tapered sludge tank is formed at the bottom of the MBR reactor.

5. The automatic off-line gas-water combined-washing membrane bioreactor (MBR) according to claim 1, characterized in that: the MBR membrane assembly is externally connected with a water producing pipe, the water producing pipe is provided with a water producing pump outside the MBR reactor, and the water producing pump is connected with the PLC automation control cabinet.

6. The automatic off-line gas-water combined-washing membrane bioreactor (MBR) according to claim 5, characterized in that: a negative pressure gauge is arranged on the water producing pipe between the MBR membrane assembly and the water producing pump, the water producing pipe externally connected with the water producing pump is provided with a water producing flowmeter, and the negative pressure gauge is connected with the PLC automation control cabinet.

7. The automatic off-line gas-water combined-washing membrane bioreactor (MBR) according to claim 1, characterized in that: a liquid level meter is arranged in the MBR reactor.

8. The automatic off-line gas-water combined-washing membrane bioreactor (MBR) according to claim 1, characterized in that: the lifting device comprises a winding engine, a diverting pulley arranged above the MBR reactor and a pulling cable connected with the MBR membrane assembly after introducing by the winding engine and passing around the diverting pulley, a travel switch is arranged at the bottom of the diverting pulley, and both the winding engine and the travel switch are connected with the PLC automation control cabinet.

* * * * *